United States Patent [19]
Fiedler

[11] Patent Number: 6,056,759
[45] Date of Patent: *May 2, 2000

[54] FLUID ACTUATED STENT DELIVERY SYSTEM

[75] Inventor: Gary R. Fiedler, Plymouth, Minn.

[73] Assignee: Schneider (USA) Inc., Plymouth, Minn.

[*] Notice: This patent is subject to a terminal disclaimer.

[21] Appl. No.: 09/122,343

[22] Filed: Jul. 24, 1998

Related U.S. Application Data

[62] Division of application No. 08/816,077, Mar. 13, 1997, Pat. No. 5,817,101.

[51] Int. Cl.[7] ........................................... A61F 11/00
[52] U.S. Cl. ................................ 606/108; 623/1; 606/191
[58] Field of Search ....................... 606/1, 108, 191–200; 623/1, 11, 12; 604/96–104

[56] References Cited

U.S. PATENT DOCUMENTS

| | | |
|---|---|---|
| 4,655,771 | 4/1987 | Wallsten . |
| 4,954,126 | 9/1990 | Wallsten . |
| 5,061,275 | 10/1991 | Wallsten et al. . |
| 5,445,646 | 8/1995 | Euteneuer et al. . |
| 5,534,007 | 7/1996 | St. Germain et al. . |
| 5,626,603 | 5/1997 | Venturelli et al. . |
| 5,707,376 | 1/1998 | Kavteladze et al. . |
| 5,817,101 | 10/1998 | Fiedler ..................................... 606/108 |

FOREIGN PATENT DOCUMENTS

WO 95/11055   4/1995   WIPO .

*Primary Examiner*—Glenn K. Dawson
*Attorney, Agent, or Firm*—Vidas, Arrett & Steinkraus, P.A.

[57] ABSTRACT

A delivery system for procuring implantation of an expandable stent in a bodily lumen of interest is disclosed including a fluid-operated moving cylinder sleeve for retaining the stent in place during delivery and retracting to release a stent at the implantation site.

14 Claims, 5 Drawing Sheets

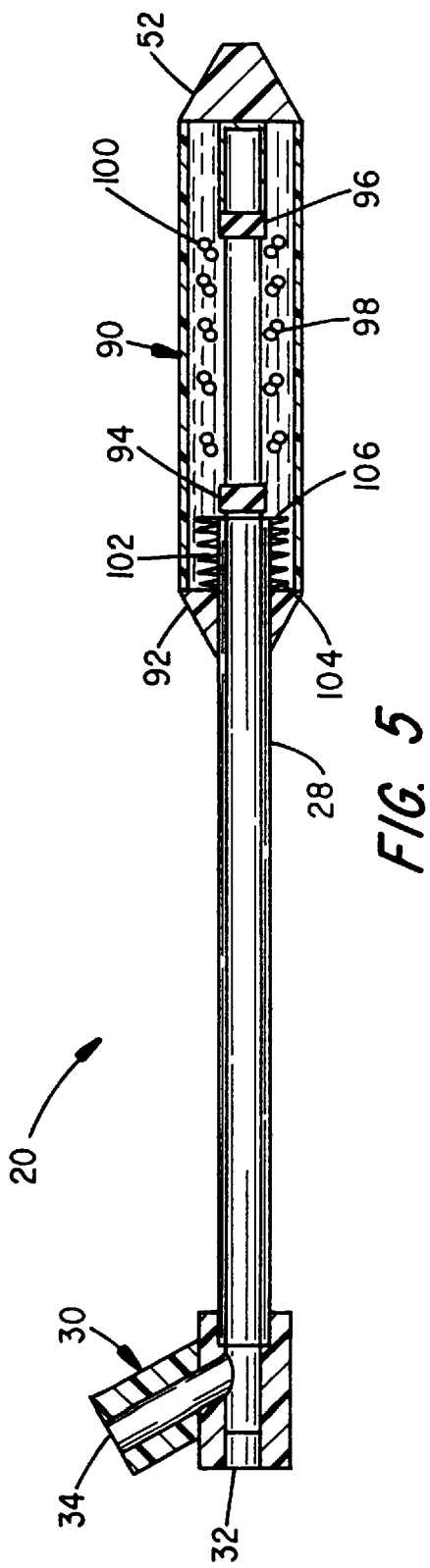
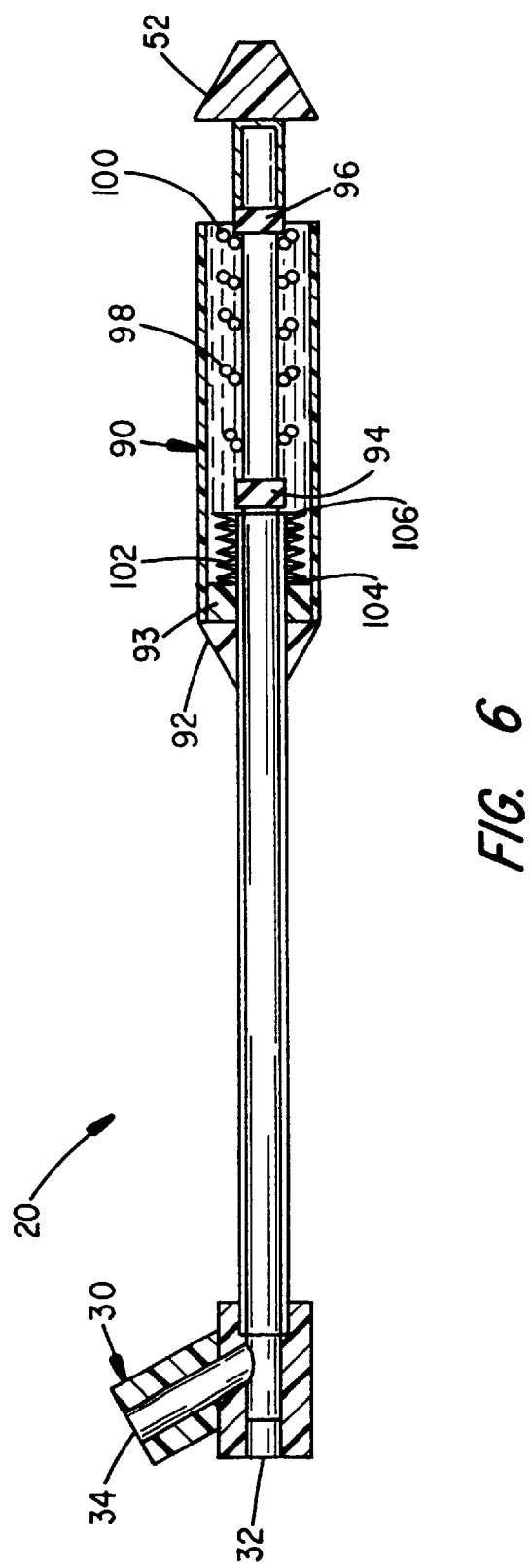

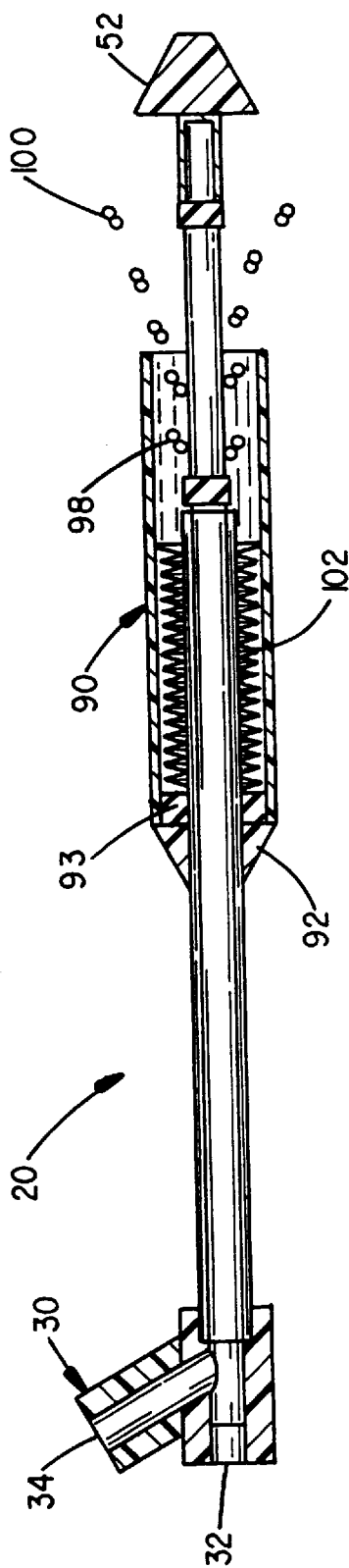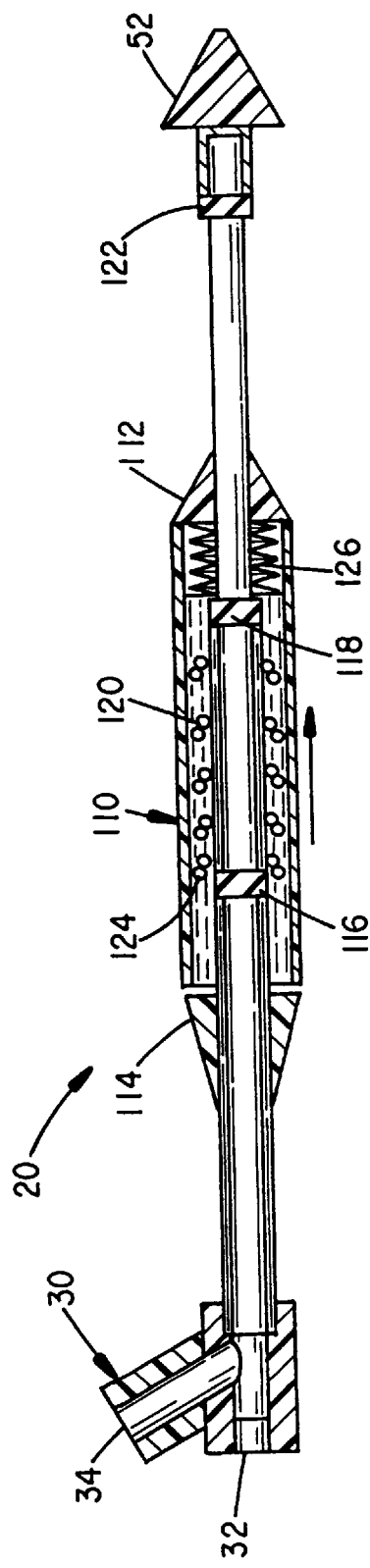

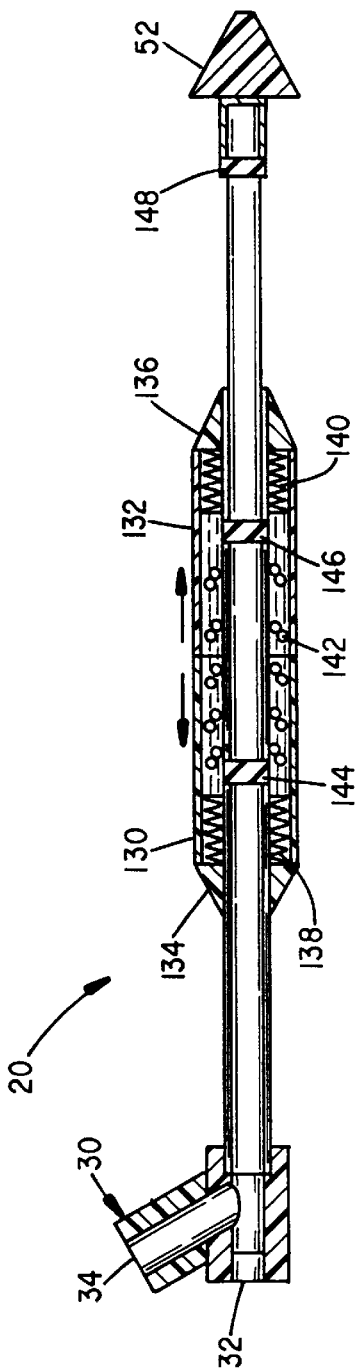
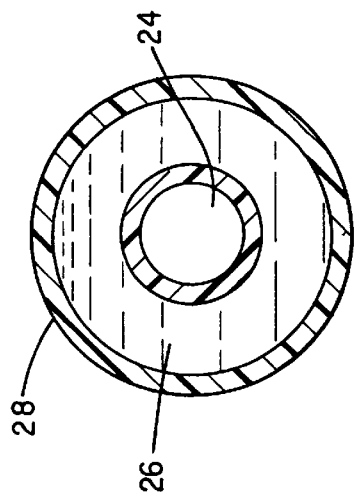
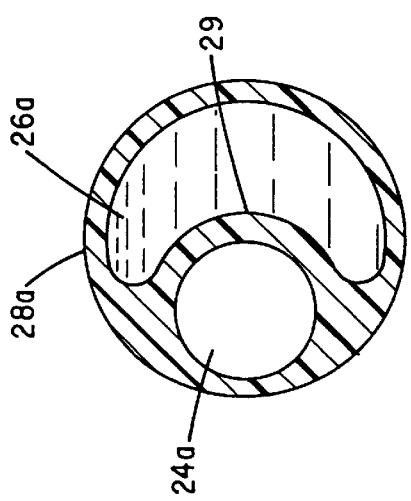

FLUID ACTUATED STENT DELIVERY SYSTEM

This application is a Divisional Application of application Ser. No. 08/816,077, filed Mar. 13, 1997, now U.S. Pat. No. 5,817,101.

BACKGROUND OF THE INVENTION

I. Field of the Invention

The present invention relates generally to the implantation of stent prostheses in body lumens and to delivery systems for transporting and accurately deploying or releasing such stents. More specifically, the invention is directed to a mechanism method for delivering and deploying a self-expanding stent utilizing a fluid-operated containment and releasing system.

II. Related Art

Auxiliary to surgical or other related invasive medicinal procedures, expandable stent implant devices are widely used in blood vessels, urinary tract ducts or other difficult to access places for the purpose of preventing restenosis, providing temporary or permanent vessel or lumen wall support or reinforcement and for other therapeutic or restorative functions. These devices are generally cylindrical or tubular in shape and are conveyed to a predetermined site or location of interest utilizing a vascular catheter, or similar transluminal device. In order to navigate the vascular system, the stents are delivered to the site constrained in a collapsed configuration or state of reduced diameter and are thereafter deployed by being released to expand or be expanded in situ. While temporary uses exist, these devices are generally designed as permanent implants which may become incorporated in the vascular or other tissue which they contact at implantation.

The stents are generally self-expanding or otherwise expanded in situ utilizing a fluid balloon or other such device. While the delivery and deployment system of the present invention can be adapted for use with either type of stent, the detailed embodiments illustrate deployment of the self-expanding variety. One well-known example of a type of self-expanding stent has become known as the Wallsten stent and is further illustrated and described in several issued U.S. patents, including Wallsten (U.S. Pat. No. 4,954,126); Wallsten (U.S. Pat. No. 4,655,771); and Wallsten et al (U.S. Pat. No. 5,061,275). (All documents cited herein, including the foregoing, are incorporated herein in their entirety for all purposes.) The Wallsten device is a woven device which has a flexible body formed of several individual flexible thread elements, each of which extends in a helix configuration with the center line of the body serving as a common axis. The elements are wound in the common direction but are displaced axially relative to each other and, under crossing a like number of elements also so axially displaced, but having the opposite direction of winding. This configuration provides a resilient braided tubular structure which assumes stable dimensions upon relaxation, but which elongates under axial tension with corresponding diameter contraction thereby enabling the stent to be mounted on a relatively small diameter catheter device and conveyed through the vascular system in a collapsed state or reduced diameter elongated configuration. As used herein, "stent" includes stent-graft and coated stents known in the art.

As indicated above, the delivery of these devices is generally accomplished by catheters of a class capable of delivering the stent to the site of interest, generally through the vascular system of the patient. Since this normally requires time consuming, torturous navigation to remote locations, improvements in the ability to accurately and easily deploy such stents once the site is reached are highly desirable.

Systems have been developed for remotely releasing the stents once the location of interest has been reached. One such system is illustrated and described in Euteneuer et al (U.S. Pat. No. 5,445,646) in which a delivery system for implantation of a self-expanding stent is disclosed which utilizes a retractable slipping sleeve system to expose a self-expanding stent held in a constrained position by bodily fluid-soluble retaining means which dissolve or swell to release the stent to radial expansion. The sleeves may be fluid operated.

While prior stent delivery systems have met with a degree of success, there remains a need for a system that will rapidly and accurately deploy a stent using distal, medial or proximal deployment. Using these terms, deployment or release is categorized according to the portion of the stent first released or expanded in situ. Delays necessitated by waiting for dissolution or expansion of retaining bands or other such constraint means require additional time which may allow unavoidable or undesirable movement of the stent, thereby reducing placement accuracy. Waiting for a delayed release system also extends the time required for the procedure.

Accordingly, it is highly desirable to provide a stent delivery system of the class described which increases the accuracy and reduces the time required for stent deployment and which, at the same time, makes the procedure easier for the operator and reduces the time required for the procedure.

It is a primary object of the present invention to provide a stent delivery and deployment system that permits rapid remote release of a stent in the location of interest.

Another object of the present invention is to provide an improved stent delivery and deployment system in which retractable deployment means also serves as the constraint means for the stent during transportation to the site of interest.

Yet another object of the present invention is to provide an improved stent delivery and deployment system which utilizes a self-retracting, extendable, improved fluid-operated release system.

Yet still another object of the present invention is to provide an improved stent delivery and deployment system which utilizes a collapsing bellows to operate the retracting device that serves as both constraint and deployment means.

Other objects and advantages of the present invention will occur to those skilled in the art upon familiarization with the descriptions and accounts contained in the specification.

SUMMARY OF THE INVENTION

By means of the present invention, there is provided a stent delivery and deployment system for procuring implantation of an expandable stent in a bodily lumen of interest. The catheter delivery and deployment system includes an elongate flexible catheter device designed to navigate the vascular system of a patient and to carry a stent retaining and deployment device attached toward the distal end of the catheter for deploying and expanding an expandable stent device, or possibly a stent-graft. The deployment system utilizes a fluid/operated retractable tubular sleeve system first as a containment or constraint device for initially retaining the stent on the catheter beneath the sleeve in a collapsed delivery configuration prior to release. Once properly aligned in situ, the tubular sleeve system is operable to retract from over the stent to release the stent distally, proximally or medially according to design of the system. In this manner, the stent can be positioned with accuracy; and at the beginning of release, should it be necessary, the stent can generally also be repositioned in the lumen.

In the detailed embodiments illustrating the invention, the catheter includes inner and outer co-axial tube members describing co-axial lumens and a constraint/release sleeve having a closed end slidably sealed about the outer co-axial tube and an open end through which a stent is released. The catheter connects proximally with a guidewire port and a fluid infusion port such that the inner co-axial lumen is a guidewire lumen and the outer lumen provides a fluid infusion lumen surrounding the inner tube.

In one embodiment, a first seal, or sliding seal, that is slidable along the outer catheter tube with respect to the sleeve is provided at the closed end of the sleeve sealing the inside of the sleeve to the outer catheter tube. A second seal, or stationary seal, that is stationary with respect to the catheter tubes, but slidable within the sleeve, is provided spaced from the first or sliding seal sealing the tube to the catheter and with the first seal defining a closed volume therebetween. The stent device is constrained by the sleeve portion extending beyond the stationary seal. Pressurized fluid infused from the outer lumen into the closed volume causes the volume to extend and the sleeve with the sliding seal to move away from the stationary seal and the stent thereby exposing and releasing the stent from the open end. The outer catheter tube may have infusion ports between the seals or it may end within the closed volume opening the lumen into the volume.

In an alternate embodiment, the outer catheter tube is connected to infuse into one or more extendable sealed bellows devices having one end which extends against a stop in the direction of the open end of the sleeve to urge the closed end of the sleeve in the opposite direction. As in the previous embodiments, the bellows can be configured to retract or collapse when the extended fluid pressure is released to urge the sleeve toward its original position in the manner of a double acting system.

BRIEF DESCRIPTION OF THE DRAWINGS

In the drawings wherein like numerals depict like parts throughout the same.

FIG. 5 depicts an alternate embodiment of the fluid operated delivery and deployment device of FIG. 1 in which the sleeve is operated by a fluid operated extendable bellows;

FIG. 6 depicts the device of FIG. 5, slightly reduced, at the beginning of the deployment or release cycle with the sleeve slightly retracted;

FIG. 7 depicts the device of FIG. 6 with the sleeve further retracted and the stent partially released;

FIG. 8 depicts an alternative embodiment of the device of FIG. 5 in which the sleeve is arranged for proximal deployment of the stent; and FIG. 9 illustrates an alternate embodiment for medial deployment of the stent utilizing a pair of oppositely disposed retractable tubular sleeve members.

FIGS. 10 and 11 are crossectional views illustrating bi-lumen and co-axial catheter construction.

DETAILED DESCRIPTION

The stent delivery and deployment system of the invention is portrayed by the several detailed embodiments which are included but which, it should be noted, are intended as examples rather than as definitive of the limitations of the scope of the invention. The system employs a retractable constraint in the form of an outer tubular sleeve or sleeves designed to perform a dual function. They are configured to retain a stent in a condition of reduced diameter otherwise defined as a delivery configuration which is required during storage and during transport or navigation through the vascular system of the patient and thereafter to axially retract from over the stent to release the stent at an implant site. With the system of the invention, a stent can be placed in situ, distal end first (distally); proximal end first (proximally); or by initially releasing and deploying the central section of the stent (medially). The deployment sleeve system can be operated as a single acting fluid actuated retractable device in which a portion of the sleeve operates with seals as an extending cylinder. In the alternative, the system can be operated using a double acting, (self-collapsing) fluid-extending bellows arrangement in which the bellows operates to retract the sleeve and release the stent and thereafter collapses to reclose the system.

Figure 1:
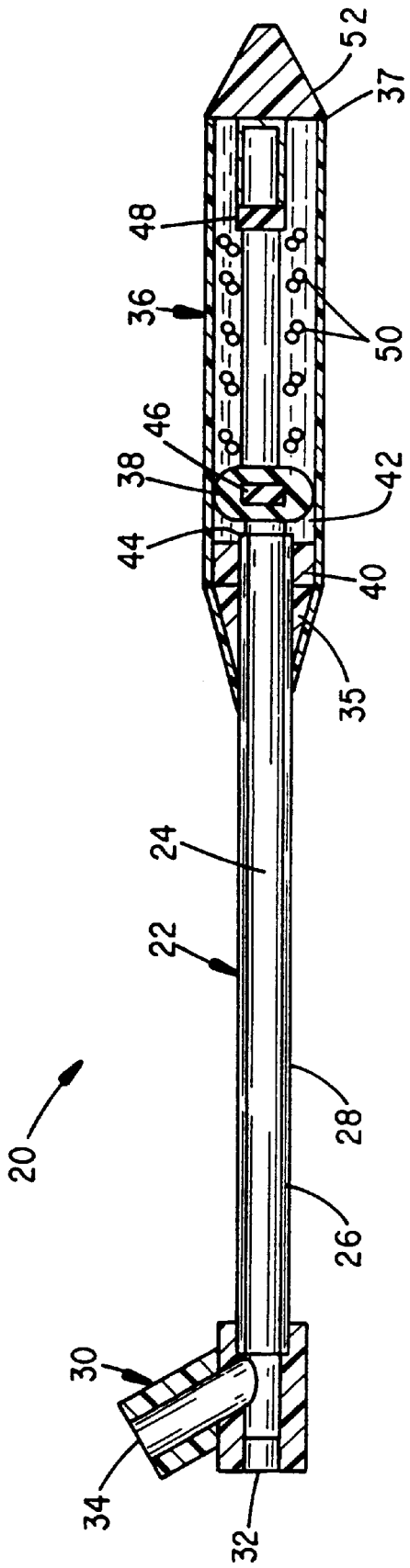
FIG. 1 depicts schematically a catheter stent delivery and deployment device in accordance with the invention, partially in section, including a fluid operated single retractable sleeve for distal release shown in the fully closed or stent retention or stent delivery disposition.
Figure 2:
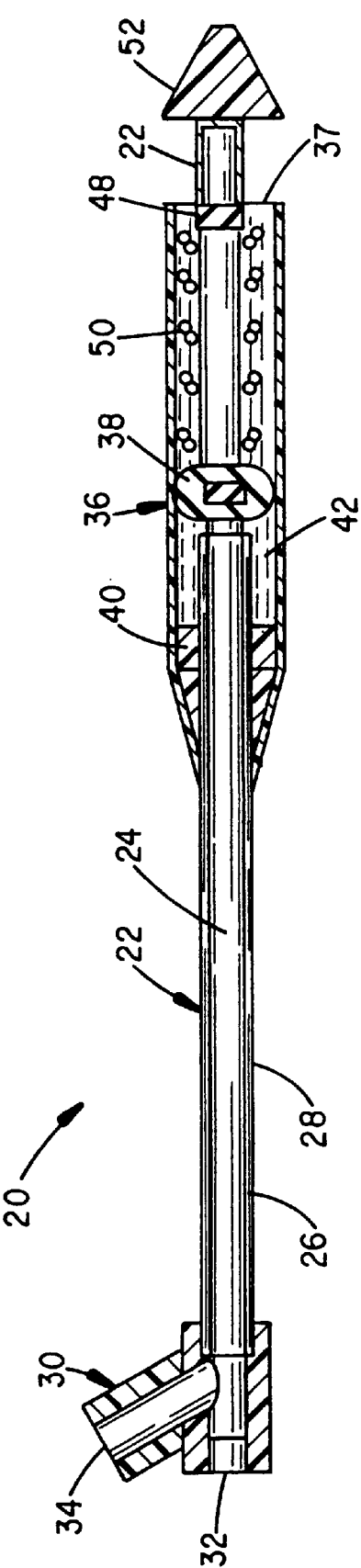
FIG. 2 depicts the device of FIG. 1, slightly reduced, at the beginning of the deployment or release cycle with the sleeve slightly retracted.
Figure 3:
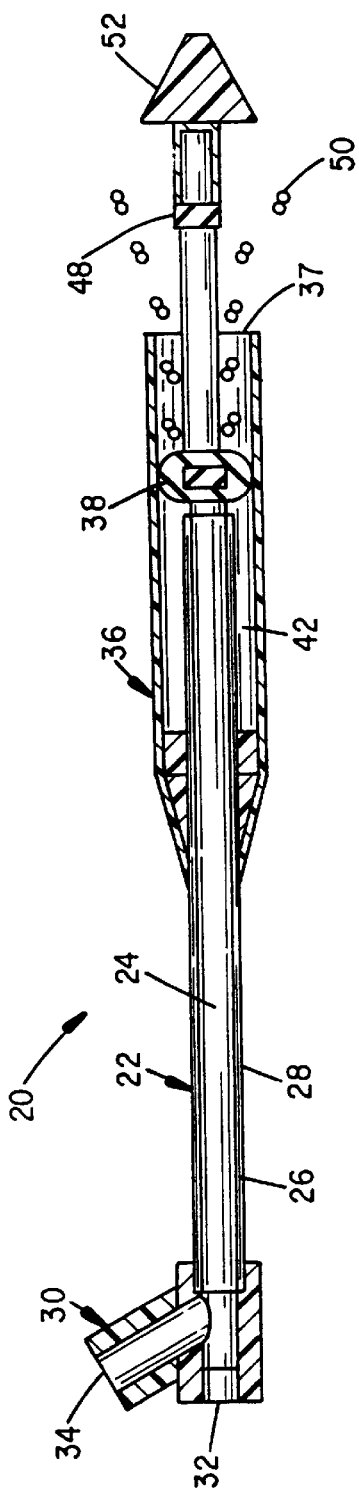
FIG. 3 depicts the device of FIG. 2 with the sleeve retracted to a larger degree and the stent partially released.

FIGS. 1–3 illustrate a fluid-operated delivery and deployment catheter system generally at 20 for distally releasing a stent. The system includes an elongated central or primary catheter tube 22 which, it will be recognized, is relatively much longer than represented in the schematic figures. The tube 22 describes a continuous internal guidewire lumen 24 extending the length of the catheter and is itself co-axially nested inside a continuous fluid supply or fluid lumen 26 of an outer or secondary catheter tube 28 for much of its length. The proximal portion of this co-axial tube system is further mounted within a valve body, generally, 30 which contains a guidewire port 32 which connects with primary or guidewire lumen 24. A hydraulic (normally saline) fluid infusion port 34 is provided in the valve body 30 that connects secondary tube fluid lumen 26 with a source of and drain for pressurized fluid for extending and collapsing a fluid-operated deployment system.

FIG. 11 illustrates in greatly magnified crossection the co-axial construction described. FIG. 10 shows an alternate positioning of the two lumens in what is known as a bi-lumen or side-by-side configuration in which the guidewire lumen 24a and the fluid lumen 26a are contained within the catheter tube 28a separated by an internal wall 29. It will be recognized that the description regarding the co-axial arrangement contained herein apply equally to a bi-lumen arrangement as well. The two arrangements are believed close enough to each other in construction that a repetition of the entire description is unnecessary to inform one skilled in the art of the interchangeability of the catheter species. Therefore, with regard to the detailed description, it is intended to apply to equivalent bi-lumen devices as well.

The distal portion of the catheter is provided with a stent-retaining sleeve member 36 which has a closed end 35 and an open end 37 and which surrounds the secondary tube 26 and is co-axially slidable therealong. The stent-retaining sleeve 36 is provided with a resilient seal means 38 which provides a liquid or fluid-tight seal between the sleeve 36 and the primary or guidewire tube 22. The seal means 38 is relatively stationary with respect to the tube 22, but slidable within the sleeve 36. The sleeve member 36 is further provided with a sliding seal at 40 which is adapted to slide along the outer surface of the secondary tube 28 with the tubular sleeve 36, but remains relatively stationary with respect to the sleeve 36 and provides a fluid-tight seal between the sleeve 36 and the secondary catheter tube 28. In this manner, the pressure seals 38 and 40 provide an extendable fluid-tight chamber 42 between the sleeve 36 and the catheter system such that pressurized fluids expelled from the distal end 44 of the secondary tube lumen 26, which preferably occurs between seals 38 and 40, will produce the desired retraction of the sleeve 36. The device also contains spaced proximal and distal radiopaque markers 46 and 48 and a stent 50 is shown assembled in the delivery or reduced diameter position. A soft distal nose or guiding cap attached to the main or primary catheter tube is shown at 52.

FIGS. 2 and 3 further illustrate the operation of the deployment arrangement of FIG. 1. In FIG. 2, the sleeve element 36 is pictured as having advanced relative to the stent in a proximal direction about as far as the location of the distal end of the stent 50 which is constrained axially between the stationary seal 38 and the radiopaque member 48. The radiopaque member 48 may be used to locate or mark the distal end of the stent fluoroscopically. In FIG. 3, the sleeve element 36 is advanced an additional distance allowing the distal end of the stent element 50 to begin to expand radially at the same time in the lumen of interest. Once the sleeve reaches the fully retracted position, the stent is fully expanded and the guiding nose member 52 can be retracted or withdrawn through the expanded stent and the catheter removed in a conventional manner. In this embodiment, when the fluid pressure is removed from the system upon deployment of the stent, the sleeve remains as it was at the end of the deployment function as the catheter is withdrawn.

Figure 4:
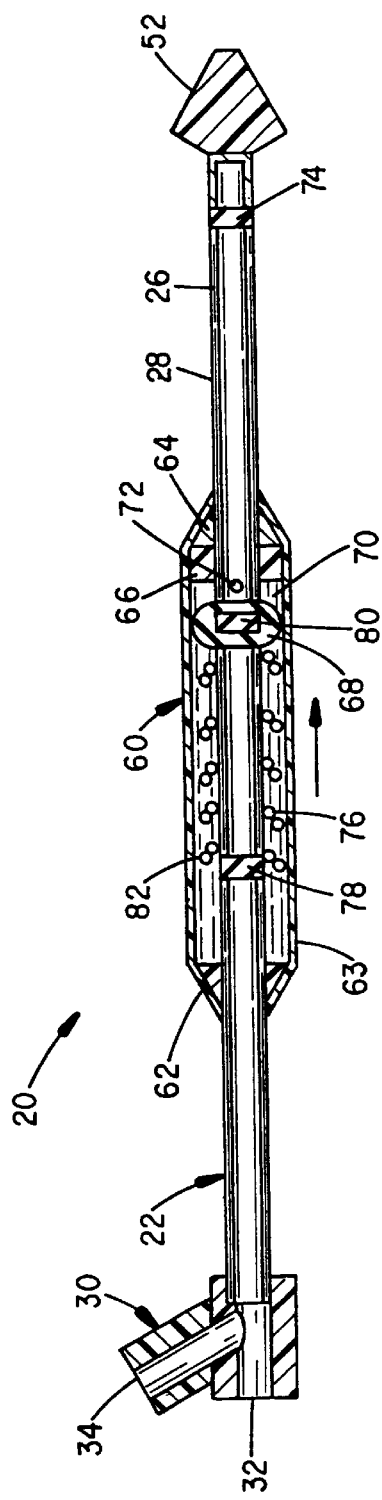
FIG. 4 depicts an alternate embodiment of the device of FIG. 1 in which the fluid operated sleeve is arranged for proximal stent deployment.

FIG. 4 depicts an alternative embodiment to that illustrated in FIGS. 1–3 in which the sleeve element 60 is mounted slightly more proximal the distal soft nose or guiding cap 52 and is flanked by a fixed proximal end taper 62 adjacent the open sleeve end 63 and distal closed end with integral sealing taper 64. A sliding seal means 66, similar to seal 40 in FIGS. 1–3, seals the distal end of the sleeve 60 about the periphery of the outer or secondary catheter tube 28. A stationary seal, similar to seal 38 in FIGS. 1–3, is provided at 68 which, with the seal 66, defines a pressurizable internal sleeve volume 70 into which pressurized fluid, normally saline solution, is infused from the lumen 26 via one or more pressure ports as at 72 located just distal the stationary seal 68. The location of the distal end of the catheter system is easily identified by radiopaque marker band 74 and the location of the exterior sliding sleeve 60 and, particularly a stent 76 within the sleeve is defined by additional flanking radiopaque marker bands 78 and 80, respectively.

The arrow indicates the direction of movement of the sleeve which operates in the same manner as the sleeve pictured in the embodiment of FIGS. 1–3. Thus, pressurized fluid infused through the lumen 26 outside the primary catheter tube 22 is infused through the pressure port or ports 72 into the volume 70 where it extends the volume forcing the sleeve 60 to move in a distal direction thereby exposing and allowing the expansion of the compressed or contained stent member 76 such that the proximal portion at 82 is the first to be released and expand with the remainder following thereafter. In this manner, precise placement or location of the proximal end of the stent may be used to define the final implant location.

A different embodiment of a sleeve system for the stent delivery and deployment system of FIG. 1 is shown in FIGS. 5–7 in which a sleeve member 90 is mounted in a manner similar to sleeve 36 of FIG. 1 at the distal end of the catheter system on the outer or secondary tubular member 28 including peripheral integral slidable proximal sealed end taper 92 (sealed by 93) and a pair of radiopaque marker bands 94 and 96 flanking constrained stent member 98 poised for distal first delivery of end 100 first. In this embodiment, however, the dual seal extendable hydraulic volume or cylinder concept of the embodiments at FIGS. 1–4 has been replaced with a normally, collapsed, extending bellows 102 operable between the integral sleeve taper 92 and a sealed stop located at the position of radiopaque marker 94. The term "bellows", as used herein, means an inflatable device that collapses on itself when deflated, but which elongates when filled with fluid. It is exemplified, but not limited to, a pleated fluid bag structure. One or more fluid ports similar to that shown at 72 in FIG. 4 is provided between the bellows 102 and the lumen 26 and the ends 104 and 106 of the bellows 102 form seals against the outer tube 28. The integral seal 93 is adapted to slide proximately upon the extension of the bellows as shown in FIGS. 6 and 7 which illustrate distal deployment of the stent 98 with end 100 expanding initially.

It should be noted in the case of the bellows-operated system that the bellows device itself may be designed to return to a collapsed position as illustrated in FIG. 5 when it is not pressurized. Thus, after deployment of the stent, the pressurized fluid can thereafter be drained from the system and the bellows allowed to collapse or retract on its own, thereby again closing the system for withdrawal through the vascular system of the patient. This feature makes it somewhat easier to withdraw the catheter inasmuch as the gap between the cap 52 and sleeve 90 is again covered. It further allows recapture of a partially deployed stent should positional adjustment be required.

FIG. 8 depicts a system similar to that of FIG. 4 for a bellows-operated system for proximal stent deployment. It includes a sleeve 110 with integral distal end taper seal 112 and matching stationary proximal end taper 114. Radiopaque markers 116 and 118 flank a constrained stent 120 and a further distal marker is shown at 122 close to the catheter guide tip 52. In this embodiment, operation of the bellows is the same as for the embodiment of FIGS. 5–7 with extension of the bellows causing the sleeve 110 to move in a distal direction thereby releasing the proximal end 124 of the stent 120 initially.

FIG. 9 illustrates the catheter equipped with an oppositely disposed pair of bellows-operated sleeve members 130 and 132 having integral oppositely disposed moveable integral end tapers 134 and 136, respectively. The sleeves 130 and 132 are respectively operated by a pair of oppositely disposed extendable bellows 138 and 140 supplied with pressurized fluid from the lumen 26 of outer tube 28 in the manner as previously described such that pressurization by fluid in the lumen 26 simultaneously pressurizes bellows 138 and 140 thereby causing concerted retraction of the sleeves 130 and 132 initially exposing a central portion of the stent 142 contained therein. Radiopaque guide markers are again provided at 144, 146 and 148. As with the other bellows-operated embodiments, relaxation of the fluid pressure in the bellows allows both bellows 138 and 140 to again collapse or retract and return the sleeves to their closed or delivery position for withdrawal of the catheter from the vascular system of the patient upon completion of implantation of the stent 142.

The materials of construction for the catheter and sleeves can be any of those conventionally employed for vascular catheter devices, or the like, including various hydrophilic, generally lubricious bio-compatible materials such as polyimides, or materials capable of being coated with hydrophilic coatings such as polyethylene or polypropylene. In addition, various nylons, urethanes and other materials may be used. The sleeve seals may be of any compatible, resilient material such as a polysiloxane rubber material.

Further with regard to the fluid supply system, it should be noted that in accordance with the invention, any suitable and compatible fluid infusion device can be employed to introduce fluid into or withdraw fluid from the port 34. One such device is a syringe-type device known as the NAMIC 13 BREEZE available from Namic Inc., Glen Falls, N.Y. The deployment system of the invention may be designed to operate at relatively elevated pressures and fluid pressures above 10 atmospheres and typically between about 14 and 25 atmospheres are generally employed.

This invention has been described herein in considerable detail in order to comply with the Patent Statutes and to provide those skilled in the art with the information needed to apply the novel principles and to construct and use such specialized components as required. However, it is to be understood that the invention could be carried out by specifically different equipment and devices, and that various modifications, both as to the equipment details and operating procedures, can be accomplished without departing from the scope of the invention itself.

What is claimed is:

1. A stent delivery system for implantation of an expandable stent in a bodily lumen of interest comprising:
   (a) an elongate flexible catheter having distal and proximal ends;
   (b) at least one fluid-operated, generally cylindrical tubular sleeve for placement over and retention of a stent in a delivery configuration prior to release, said sleeve being axially adjustable relative to said catheter and said stent and having a closed end and an open end for release of a contained stent;
   (c) an expandable stent having a proximal and distal end and being collapsible about said catheter to a delivery configuration of reduced diameter along the length thereof;
   (d) fluid supply system for supplying infusing fluid into said sleeve; and
   (e) integral fluid driven operating mechanism for axially adjusting said sleeve along said catheter, wherein said closed end includes a first seal between said catheter and said sleeve and moveable with respect to said catheter and a second seal between said catheter and said sleeve spaced from said first seal and moveable with respect to said sleeve and a fluid infusion port in said catheter for infusing pressurized fluid between said seals for causing said sleeve to move in the direction of said closed end.

2. The system of claim 1 wherein said stent is a self-expanding stent.

3. The system of claim 1 wherein said open end of said sleeve is the distal end of said sleeve.

4. The system of claim 1 wherein the open end of said sleeve is the proximal end.

5. The system of claim 1 wherein said catheter is provided with inner and outer co-axial tube members describing co-axial inner and outer lumens, said outer lumen terminating between said first and said second seals in said sleeve such that fluid infused through said outer lumen outside said inner tube can be used to axially adjust said sleeve.

6. The system of claim 5 wherein said open end of said sleeve is the distal end of said sleeve.

7. The system of claim 5 wherein the open end of said sleeve is the proximal end.

8. The system of claim 5 wherein said stent is a self-expanding stent.

9. The system of claim 1 wherein said catheter is provided with side-by-side guidewire and fluid lumens, said fluid lumen having an outlet between said first and said second seals in said sleeve such that fluid infused through said fluid lumen can be used to axially adjust said sleeve.

10. The system of claim 9 wherein said open end of said sleeve is the distal end of said sleeve.

11. The system of claim 9 wherein the open end of said sleeve is the proximal end.

12. The system of claim 9 wherein said stent is a self-expanding stent.

13. A method of deploying an expandable stent in a bodily lumen of interest for procuring implantation of the stent comprising the steps of:
   a. providing an elongate flexible vascular catheter having distal and proximal ends; a stent in a delivery configuration of reduced diameter on said flexible catheter near the distal end thereof; and a fluid-operated, generally cylindrical tubular sleeve over the mounted stent, said sleeve providing retention of said stent in said delivery configuration and having an internal operator operable to axially adjust said sleeve relative to the catheter to release said stent;
   b. intraluminally disposing said catheter to place said stent at a deployment site of interest; and
   c. infusing fluid into said internal operator in said sleeve to retract said sleeve axially in a direction to release said stent in situ.

14. The method of claim 13 wherein said stent is self-expanding and including the step of removing said vascular catheter by reversing step (b) and withdrawing the distal end of said catheter through said stent after expansion of said stent.

* * * * *